(12) United States Patent
Mitterer et al.

(10) Patent No.: US 6,579,723 B1
(45) Date of Patent: Jun. 17, 2003

(54) METHOD OF RECOVERING HIGHLY PURIFIED VWF OR FACTOR VIII/VWF-COMPLEX

(75) Inventors: Artur Mitterer, Mannsdorf (AT); Christian Fiedler, Vienna (AT); Bernhard Fischer, Vienna (AT); Friedrich Dorner, Vienna (AT); Johann Eibl, Vienna (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/367,362

(22) PCT Filed: Feb. 18, 1998

(86) PCT No.: PCT/AT98/00033

§ 371 (c)(1), (2), (4) Date: Oct. 21, 1999

(87) PCT Pub. No.: WO98/38218

PCT Pub. Date: Sep. 3, 1998

(30) Foreign Application Priority Data

Feb. 27, 1997 (AT) ................................. 339/97

(51) Int. Cl.[7] ............................ G01N 1/18; G01N 33/86
(52) U.S. Cl. ...................... 436/177; 436/18; 436/161; 436/162; 436/174; 436/175; 436/176; 436/177; 436/178; 436/824; 436/69; 435/7.1; 435/7.2; 435/272; 435/288.6; 435/803; 530/380; 530/381; 530/383; 530/412; 530/413; 530/418; 530/427; 422/56; 422/59; 422/70; 422/73; 422/101
(58) Field of Search ................................. 530/380, 381, 530/383, 412, 413, 418, 427; 435/7.1, 7.2, 272, 288.6, 803; 436/18, 161, 162, 174, 175–178, 824; 422/56, 59, 70, 73, 101

(56) References Cited

U.S. PATENT DOCUMENTS

| 4,361,509 A | 11/1982 | Zimmerman et al. ... 260/112 B |
| 4,670,543 A | 6/1987 | Bourgois et al. ............ 530/383 |
| 4,774,323 A | 9/1988 | Newman et al. ............ 530/383 |

(List continued on next page.)

FOREIGN PATENT DOCUMENTS

| CA | 2251558 | 10/1997 | ......... C07K/14/755 |
| CA | 2009946 | 4/2000 | ......... C07K/14/745 |
| EP | 0 295 645 A2 | 12/1988 | |

(List continued on next page.)

OTHER PUBLICATIONS

Hajos et al., Histidine as a dipolar eluent component in cation chromatography, Journal of Chromatography 789/1–2: 141–148 (1997).*

Official Action of Sep. 2, 1997 issued with respect to Austrian priority application A 339/97 (translation).

(List continued on next page.)

*Primary Examiner*—Long V. Le
*Assistant Examiner*—Gailene R. Gabel
(74) *Attorney, Agent, or Firm*—Townsend and Townsend and Crew LLP (57) ABSTRACT

A method for purifying factor VIII/vWF complex or free vWF by immunoaffinity chromatography in a form suitable for use as a medicament. Factor VIII/vWF complex or free vWF is recovered from an immunoaffinity adsorbent by using an eluting agent containing a zwitterionic species. The presence of the zwitterionic species allows for the use of mild conditions throughout the preparation, facilitating retention of molecular integrity, activity, and incorporation of the recovered proteins into pharmaceutical preparations without the need for additional stabilizers or preservatives.

51 Claims, 1 Drawing Sheet

Gel filtration analysis of the FVIII/vWF-complex

U.S. PATENT DOCUMENTS

| | | | |
|---|---|---|---|
| 5,006,642 A | | 4/1991 | Newman et al. ............. 530/383 |
| 5,506,341 A | * | 4/1996 | Newman et al. ............. 530/383 |
| 5,710,254 A | * | 1/1998 | Newman et al. ............. 530/383 |
| 5,869,617 A | | 2/1999 | Fischer et al. ............... 530/381 |
| 5,877,152 A | | 3/1999 | Fischer et al. ................. 514/12 |
| 5,880,265 A | | 3/1999 | Fischer et al. ............... 530/383 |
| 6,103,693 A | * | 8/2000 | Fischer et al. ................. 514/12 |
| 6,228,613 B1 | | 5/2001 | Fischer et al. ............. 435/69.1 |

FOREIGN PATENT DOCUMENTS

| | | |
|---|---|---|
| EP | 0 469 985 A1 | 2/1992 |
| EP | 0 600 480 A2 | 6/1994 |
| WO | WO 82/04395 | 12/1982 |
| WO | WO 91/18017 | 11/1991 |
| WO | WO 93/22336 | 11/1993 |
| WO | WO 96/10584 | 4/1996 |
| WO | WO 97/34930 | 9/1997 |
| WO | WO 97/39033 | 10/1997 |

OTHER PUBLICATIONS

International Search Report for PCT/AT98/00033, dated Jun. 30, 1998.

Tajima, Y. et al., "Purification of Blood Coagulation Factor VIII by Affinity Chromatography Using Monoclonal Antibody" *Chem. Abstracts*, vol. 112, 1990, p. 386, 135586x.

Weinstein, R.E., "Immunoaffinity Purification of Factor VIII", *Chem. Abstracts*, vol. 110, 1989, p. 402, 198998n.

Zimmerman, T.S., "Purification of Factor VIII by Monoclonal Antibody Affinity Chromatography", *Chem. Abstracts*, vol. 109, 1988, p. 282, 34300g.

Hornsey, V.S. et al., "Immunoaffinity Purification of Factor VIII Complex", *Chem. Abstracts*, vol. 107, 1987, p. 562, 57015r.

Croissant, M.P. et al., "Characterization of Four Monoclonal Antibodies to Factor VIII Coagulant Protein and their Use in Immunopurification of Factor VIII", *Chem. Abstracts*, vol. 106, 1987, p. 300, 151939w.

Rotblat, F. et al., "Purification of Human Factor VIII:C and its Characterization by Western Blotting Using Monoclonal Antibodies", *Chem. Abstracts*, vol. 103, 1985, p. 341, 67820f.

Holmberg, L. and Ljung, R., "Purification of F.VIII:C by Antigen–antibody Chromatography", *Chem. Abstracts*, vol. 89, 1978, p. 248, 55806k.

Fischer, B. et al., "Structural Analysis of Recombinant von Willebrand Factor: Identification of Hetro– and Homo–dimers", *FEBS*, vol. 351, 1994, pp. 345–348.

Furlan, M. et al., "Triplet Structure of von Wildebrand Factor Reflects Proteolytic Degradation of High Molecular Weight Multimers", *PNAS*, vol. 90, 1993, pp. 7503–7507.

Goodall, A.H. and Meyer, D., "Registry of Monoclonal Antibodies to Factor VIII and von Willebrand Factor" *Thromb. and Haem.*, vol. 54, 1985, pp. 878–891.

Hornsey, V.S. et al., "Immunoaffinity Purification of Factor VIII Complex", *Thromb. and Haem.*, vol. 57, 1987, pp. 102–105.

Karlsson, R., "Real–Time Competitive Kinetic Analysis of Interactions Between Low–Molecular–Weight Ligands in Solution and Surface–Immobilized Receptors", *Anal. Biochem.*, vol. 221, 1994, pp. 142–151.

Malmqvist, M., "Biospecific Interaction Analysis Using Biosensor Technology", *Nature*, vol. 361, 1993, pp. 186–187.

Mejan, O. et al., "Immunopurification of Human Factor VIII/vWF Complex from Plasma", *Thromb. and Haem.*, vol. 59, 1988, pp. 364–371.

Tsang, V.C.W. and Wilkins, P.P., "Optimum Dissociating Condition for Immunoaffinity and Preferential Isolation of Antibodies with High–Specific Activity", *J. of Immunol. Methods*, vol. 138, 1991, pp. 291–299.

Wood, W.I. et al., "Expression of Active Human Factor VIII from Recombinant DNA clones", *Nature*, vol. 312, 1984, pp. 330–337.

* cited by examiner

FIG. 1

Gel filtration analysis of the FVIII/vWF-complex

METHOD OF RECOVERING HIGHLY PURIFIED VWF OR FACTOR VIII/VWF-COMPLEX

FIELD OF THE INVENTION

The invention relates to a method of recovering a highly purified vWF or a factor VIII/vWF-complex, respectively, from a biological starting material by means of immunoaffinity chromatography, as well as to a stable preparation containing highly purified vWF or factor VIII/vWF-complex.

BACKGROUND

Blood coagulation is a complex process including the sequential interaction of a series of components, in particular of fibrinogen, factor II, factor V, factor VII, factor VIII, factor IX, factor X, factor XI and factor XII. The loss of one of these components or the inhibition of its functionality causes an increased tendency of blood coagulation which may be life-threatening in some patients.

Von Willebrand factor (vWF) circulates in plasma complexed with factor VIII, factor VIII aiding blood coagulation and vWF in the complex with factor VIII stabilising the latter and protecting it from proteolytic degradation. On account of its function in the platelet aggregation, vWF also directly interferes in blood coagulation. vWF exists in plasma in a series of multimer forms of a molecular weight of from $1 \times 10^6$ to $20 \times 10^6$ Dalton. vWF is a glycoprotein primarily formed in the endothelial cells of mammals and subsequently liberated into circulation. In this connection, starting from a polypeptide chain having a molecular weight of approximately 220 kD, a vWF dimer having a molecular weight of 550 kD is formed in the cells by the formation of several sulfur bonds. Thereupon, further polymers of the vWF with ever increasing molecular weights, up to 20 million Dalton, are formed from the vWF dimers by linking. It is presumed that particularly the high-molecular vWF multimers have an essential importance in blood coagulation.

In hemophilia, blood coagulation is disturbed by a deficiency of certain plasmatic blood coagulation factors. In hemophilia A, the bleeding inclination is caused by a deficiency of factor VIII or a deficiency of vWF, respectively, which constitutes an essential component of factor VIII. Treatment of hemophilia A is effected primarily by substituting the lacking coagulation factor with factor concentrates, e.g. by infusion of factor VIII, factor VIII-complex or vWF.

vWF syndrome has several clinical pictures caused by an underproduction or an overproduction of vWF. Thus, an overproduction of vWF causes an increased thrombosis tendency. An undersupply caused by the absence or reduction of high-molecular forms of vWF is manifested in an increased bleeding tendency and an increased bleeding time on account of the inhibition of platelet aggregation and of wound closure.

A vWF deficiency may also cause a phenotypic hemophilia A, since vWF is an essential component of functional factor VIII. In these instances, the half-life of factor VIII is reduced to such an extent that its function in the blood coagulation cascade is impaired. Patients suffering from von Willebrand syndrome (vWD) thus frequently exhibit a factor VIII deficiency. In these patients, the reduced factor VIII activity is not the consequence of a defect of the X chromosomal gene, but an indirect consequence of the quantitative and qualitative change of vWF in plasma. The differentiation between hemophilia A and vWD may normally be effected by measuring the vWF antigen or by determining the ristocetin-cofactor activity. Both the vWF antigen content and the ristocetin cofactor activity are lowered in most vWD patients, whereas they are normal in hemophilia A patients.

Conventional methods for a therapy of von Willebrand syndrome use vWF recovered from plasma, and there are a number of attempts to treat vWD patients with purified vWF or factor VIII/vWF-complex. The development of monoclonal and polyclonal antibodies to blood factors, in particular to vWF, has enabled an improved isolation and purification of vWF or of factor VIII/vWF-complex from plasma or other biological sources.

Purification of factor VIII and of factor VIII/vWF-complex, respectively, from plasma is particularly rendered difficult by the fact that factor VIII occurs only in very small amounts in plasma, is extremely labile, and that the association of factor VIII with vWF is reversible under specific conditions.

By expressing factor VIII in recombinant cells (Wood et al., Nature 312: 330–337, 1984), it has been possible to prepare factor VIII by genetic engineering, yet it was only by the addition of or coexpression with vWF that a commercially usable yield of recombinant factor VIII could be achieved. Likewise, vWF has been prepared by genetical engineering methods and expressed in recombinant cells (Fischer et al., 1994, FEBS Letters 351: 345–348).

The recovery of purified factor VIII, vWF or factor VIII/vWF-complex from plasma or of factor VIII or vWF, respectively, from recombinant cells by means of various purification methods has also been described.

Zimmerman et al. (U.S. Pat. No. 4,361,509) describe a method of purifying factor VIII, wherein factor VIII/vWF complex is bound to a monoclonal anti-vWF antibody, and factor VIII is dissociated from the complex by means of $CaCl_2$ ions. The thus obtained factor VIII subsequently is recovered in pure state via a further chromatographic step. The immunoaffinity carrier to which vWF is still adsorbed is regenerated by means of a chaotropic agent, in particular NaSCN, a vWF/NaSCN solution being incurred as a by-product and being discarded.

U.S. Pat. No. 5,006,642 describes the recovery of vWF from a solution that comprises vWF and a chaotropic agent and is incurred as a by-product according to U.S. Pat. No. 4,361,509, by dialysis against a suitable buffer or by desalting the solution in a further chromatographic step.

EP 0 383 234 describes the preparation of a vWF concentrate by means of anion exchange chromatography, wherein a factor VIII/vWF-complex contained in a solution is dissociated by the addition of a calcium- and amino acid-containing buffer, and a vWF concentrate is recovered.

EP 0 469 985 describes a method of preparing vWF from plasma cryoprecipitate, which is largely free from factor VIII, in which vWF is separated from factor VIII in a first purification step, wherein factor VIII binds to an anion exchanger, whereas vWF is not bound. In a second step, the salt concentration of the vWF-containing eluate is reduced, whereby vWF can bind to a second anion exchanger. Thereafter vWF is eluted by increasing the ionic strength.

A purified vWF which optionally is complexed with factor VIII is desirable for use in the therapy of patients afflicted with von Willebrand syndrome, but also of patients suffering from phenotypic hemophilia A. Furthermore, due to the stabilizing effect of vWF, a better storage stability of factor VIII preparations is attained.

To purify factor VIII/vWF-complex, it has been suggested to precipitate contaminating proteins, such as, e.g., fibrinogen, by means of high concentrations of amino acids, in particular glycine (WO 82/04395, EP 0 383 234).

EP 0 600 480 describes the purification of factor VIII/vWF-complex from plasma by means of a combination of anion/cation exchange chromatography, wherein the factor VIII/vWF-complex is stabilized with heparin and optionally lysine is added as an antiprotease.

EP 0 295 645 describes the purification of factor VIII/vWF-complex on an affinity matrix, wherein specific peptides binding to vWF are used as the affinity carrier, the complex binding to these peptides and subsequently being eluted with a pH gradient.

WO 96/10584 describes a method of recovering highly-purified recombinant vWF by means of a combined anion exchange/heparin-affinity chromatography, and EP 0 705 846 describes the separation between high- and low-molecular fractions of vWF.

Mejan et al. (1988, Thromb. Haemost. 59: 364–371) have suggested to purify factor VIII/vWF-complex from plasma by means of immunoaffinity. By using a vWF-specific antibody coupled to a carrier, factor VIII/vWF-complex is bound to the carrier under physiological conditions, and the complex is elated under alkaline conditions at a pH of 10.2. To neutralize the alkaline environment, the eluate is immediately admixed with 2 M of acetic acid, stabilized with human serum albumin and subsequently lyophilized. The weakly alkaline elution environment was particularly chosen so as to prevent a dissociation of factor VIII/vWF-complex and an inactivation of factor VIII.

However, it has been emphasized repeatedly that a particular difficulty in purifying the complex consists in maintaining the association of the proteins, since the complex of the two components is unstable. With their method, Mejan et al. (1988, Thromb. Haemost. 59: 364–371) achieved a 50% recovery of the factor VIII/vWF complex with a specific activity of factor VIII≧20 U/mg and vWF≧20 U/mg. Under the elution conditions described, however, a partial liberation of the antibodies from the column has been observed, leading to a contamination of the eluate with approximately 90 ng/ml eluate on murine IgG. The antibodies thus had to be removed by a further chromatographic step.

Hornsey et al. (1987, Thromb. Haemost. 57: 102–105) examined the influence of different eluting agents in the immunoaffinity purification of factor VIII/vWF-complex and found that chaotropic agents, such as potassium iodide and lithium diiodosalicylates are particularly effective as eluting agents. The eluting agent used furthermore contained calcium chloride/ions as well as 1 M lysine for stabilizing the factor VIII and vWF activities. It has been observed that the high concentration of the amino acid protects the proteins from the denaturing effect of the chaotropic agent. Under the elution conditions used it was found that the final product was contaminated with the immunoadsorbent, here mouse monoclonal vWF antibodies, up to 30 ng/ml (approximately 300 ng/mg protein). On account of its high toxicity, the chaotropic desorption agent also had to be removed from the product by means of an additional purification step. By means of the immunoaffinity chromatography, Hornsey et al. (1987, Thromb. Haemost. 57: 102–105) obtained a yield of 57% factor VIII:C and 44% vWF, and a specific activity of 45 U of factor VIII and 60 U of ristocetin activity/mg protein.

Although the immunoaffinity is one of the preferred methods for the purification of vWF or of factor VIII/vWF-complex, the greatest disadvantage in the use of the immunoaffinity chromatography is the possible contamination of the final product with the immunoadsorbent, as well as the necessary regeneration of the affinity matrix used. The strong binding between antibody and vWFor factor VIII/vWF complex, respectively, frequently makes it necessary to use a strong desorption agent, such as, e.g., a chaotropic agent. By this, not only the activity and the molecular structure of vWF or of the factor VIII/vWF-complex are impaired, but due to a continuous liberation of antibodies from the carrier it also leads to a leakage of the immuno-carrier. The half-life of the affinity carrier is strongly reduced, and its multiple usability is impaired. Since particularly for the commercial preparation of vWF or factor VIII/vWF-complex the use of immunoaffinity columns is very expensive, it would thus be desirable to provide a method which does not have these disadvantages.

SUMMARY

It is thus the object of the present invention to provide an improved method of recovering vWF or factor VIII/vWF-complex by means of immunoaffinity chromatography, which does not have the disadvantages described above.

According to the invention, this object is achieved in that a method is provided in which vWF or a factor VIII/vWF-complex is purified by means of immunoaffinity chromatography, wherein a vWF or a factor VIII/vWF-complex bound to an immunoadsorbent is eluted by means of an eluting agent containing a zwitterion as a substantial active component.

As the zwitterions in the eluting agent, according to the present invention e.g. amino acids or analogues of amino acids can be used, whose isoelectric range lies between 3.2 and 9.6, and which are present as zwitterions in the neutral pH range. Therein, the preferred zwitterions are selected from the group of neutral amino acids or analogues of amito acids, preferably alanine, β-alanine, 2-amino-butyrid acid, 4-amino-butyric acid, asparagine, citrulline, glutamine, glycine, histidine, isoleucine, leucine, methionine, phenylalanine, proline, sarcosine, serine, taurine, threonine, tryptophane and tyrosine, or betaines or analogues thereof, in particular sulfobetaines.

Particularly preferred for carrying out the method are the amino acids alanine, β-alanine, glycine, histidine, phenylalanine or betaine. According to the present method, the zwitterions may be present in an aqueous solution at a concentration of between 0.01 and 0.5 M, preferably between 0.08 and0.2 M, particularly preferred between 0.1 and 0.15 M. There, aqueous solutions may be solutions which exclusively consist of water and do not contain any further additives.

According to the present method, the eluting agent containing the zwitterion may have a physiological pH, preferably a pH of between 6.5 and 8.0, especially preferred between 7.0 and 7.8, particularly preferred of 7.4. In this pH range, all the above-mentioned amino acids or analogues thereof are electrically neutral and present as zwitterions.

The eluting agent may be prepared by simply dissolving the amino acid or the analogue of an amino acid with the desired molarity in water. Since the pH and the ionic strength do not change or change only unsubstantially due to the neutral charge of the zwitterion, an adjustment of a pH or of the ionic strength is not necessarily required. Since in some instances an additonal stabilization of the eluate containing the vWF or the vWF-complex is desirable, e.g. if one or several virus inactivation steps are carried out, as further substances optionally sugar, such as sucrose, or maltose, can be added as stabilizers. Since these sugars also are chemically/physically neutral, an additon thereof does not change the pH of the eluting agent.

The use of amino acids, such as, e.g., glycine, histidine, or arginine as a precipitating agent, antiprotease or stabilizer or for an improved reconstitution of factor VIII solutions has,e.g., been described in EP 0 383 234 or in EP 0 600 480, the concentration of the amino acids used lying between 0.5–3 M. Moreover, amino acids have been known as a component of eluting agents or buffers in chromatographic methods. Tsang et al. (1991, J. Immunol. Methods 138: 291–299) have examined various dissociation conditions of antigens bound to immunoaffinity matrices and have found chaotropic agents to be the most effective dissociation reagents for breaking up antigen-antibody bonds. However, the specific activity of the eluted proteins was low on account of the denaturing effect of the chaotropic agents. The use of 0.5 M glycine, pH 2.0, as eluting reagent exhibited a comparatively low dissociation capacity and a relatively low specific activity of the protein recovered. The low pH of the eluting agent furthermore made it necessary to neutralize the eluate rapidly so as to avoid a further loss of activity of the protein. Likewise it has been found that antibodies detach from the carrier under these conditions and get into the eluate.

On account of what has been observed by Tsang et al. (1991, J. Immunol. Methods 138: 291–299) it has been the more surprising that it has been found within the scope of the present invention that an eluting agent containing a zwitterion as an essential active eluting reagent is capable of effectively dissociating an antibody/antigen complex under mild conditions and in the neutral pH range and without the use of chaotropic agents. On account of the mild elution conditions, the desired antigen is not only efficiently obtained in purified form and, on account of the high specificity to the antibody, free from contaminating components, but it can also be recovered substantially free from immunoadsorbent, since a dissociation of the antibody-antigen-complex does occur, yet the binding of the antibody to the carrier is not affected, and the antibody remains in stable association with the carrier.

To carry out the method according to the invention, as the ligand, any immunoadsorbent having a binding specificity to vWF, and capable of being immobilized on a solid carrier as ligand, may be used.

According to one embodiment of the method of the invention, an anti-vWF-antibody is used as the immunoadsorbent. The antibody used may be polyclonal or monoclonal. Monoclonal antibodies are, however, particularly preferred. To carry out the method according to the invention, all the known anti-vWF-antibodies may be used, e.g. such as have been described by Goodall et al. (Thromb. Haemost. 54: 878–891, 1985). Preferably, a monoclonal vWF antibody from a hybridoma, selected from the series of cell hybridisations of murine myeloma X63 and splenocytes of BALB/C mouse, immunized with factor VIII/vWF-complex, as, e.g., described in EP 0 179 006, is used.

According to a preferred embodiment, as the ligand for carrying out the method of the invention, a fragment of an anti-vWF-antibody that binds vWF or factor VIII/vWF-complex, respectively, is used. Particularly preferred is the F'ab-fragment of a vWF antibody. Using a fragment of a specific antibody has the advantage that an affinity carrier matrix with the antibody fragment as the ligand can be prepared in a simple manner, whereby, due to the small molecular size of the ligand, the antigen binding capacity and the binding efficiency of the carrier can be increased. Also the risk of a contamination of the product by a complete antibody possibly getting into the eluate is greatly reduced and thus negligible.

The immunoadsorbent preferably is immobilized on a carrier, wherein all the known natural or synthetic insoluble polymers suitable for affinity chromatography can be used as the carrier.

The method according to the invention constitutes a simple and efficient method of recovering vWF or factor VIII/vWF-complex having a high specific activity and in a high yield from an optionally not pre-purified protein solution. Any biological solution, e.g. plasma, a plasma pool, a plasma fraction, a cryoprecipitate, the supernatant of a cell culture expressing recombinant vWF or factor VIII or co-expressing factor VIII and vWF, respectively, or a pre-purified protein solution may be used as the starting material containing vWF or a factor VIII/vWF-complex. The present invention is, however, particularly suitable for recovering vWF or factor VIII/vWF-complex from non-pre-purified protein solutions, e.g. directly from plasma or from the supernatant of a recombinant cell culture. According to the present invention, vWF or factor VIII/vWF-complex contained in a starting material is bound to the immunoadsorbent, preferably under physiological conditions. There, the starting solution is adjusted to a pH of between 6.5 and 7.8, at a temperature of between 4° C. and 20° C., and is contacted with the immunoadsorbent, whereby, on account of the specific binding capacity of the antibody to vWF, vWF or factor VIII complexed with vWF, respectively, is bound, whereas other proteins contained in the solution are not bound and thus are separated in a simple manner from vWF or from factor VIII/vWF-complex.

By means of the method according to the invention and elution with a buffer in the neutral pH range, containing a zwitterion as an essential eluting agent, vWF or factor VIII/vWF-complex can be recovered from the immunoadsorbent with a particularly high efficiency. On account of the specific interaction of vWF and factor VIII in a complex, also factor VIII complexed with vWF is bound, whereas free, non-complexed factor VIII cannot bind to the immunoadsorbent. By aid of the method according to the invention, thus a pure vWF or factor VIII complexed exclusively with vWF, respectively, is recovered. It has particularly been found that approximately 85% of the vWF or of the factor VIII/vWF-complex present in the starting material can be recovered. Thus, by means of the method according to the invention, vWF or factor VIII/vWF complex, respectively, is recovered in a purity of more than 90%, preferably of more than 95%. This high recovery rate and purity has not been attained by means of the hitherto described chromatographic methods in one method step. Moreover, the use of the eluting agent described and the mild eluting conditions have the advantage that the association of factor VIII with vWF, and thus the physiological and molecular structure of the complex, are retained.

The method according to the invention has the further particular advantage that before and during the elution, a change of the pH of the solution containing the proteins is not necessary and the biological activity of the protein to be purified is not impaired by a change of the pH.

By using the above-described eluting agents, the vWF or the vWF-complex, respectively, is efficiently desorbed from the immunoadsorbent, without impairing the structural integrity of the vWF and the activities of the vWF or factor VIII. The intactness of the structural integrity of vWF was particularly proved by vWF multimer analysis, as, e.g., described in EP 0 705 846, before adsorption and after elution from the immunocarrier. Likewise it has been shown that the collagen binding activity as well as the specific platelet agglutination activity of the vWF substantially is not impaired.

A comparison of the factor VIII:Ag to the factor VIII:C-activity in the starting material and after elution from the carrier showed that the ratio does not change. The specific activity preferably is >80 U/mg.

The highly purified vWF or factor VIII/vWF-complex obtained with the method according to the invention may likewise be further purified by chromatographic methods known from the prior art, such as ion exchange, affinity or gel filtration chromatography. Purified factor VIII/vWF-complex may, e.g., be adsorbed to an affinity carrier that, specifically binds either vWF or factor VIII, and the proteins may be recovered separately from each other and in free form by means of a buffer which dissociates the complex, e.g. a buffer having a low pH, a high ionic strength, and containing $CaCl_2$ or NaCl. With this procedure it is possible to selectively recover free factor VIII which is not complexed with vWF, or vWF not complexed with factor VIII, respectively. The thus isolated proteins or antigens are particularly characterized by not being impaired in terms of their vWF binding or their factor VIII binding, respectively. By this it is possible to purposefully recover highly purified factor VIII having a high vWF binding specificity, or highly purified vWF having a high factor VIII binding specificity, respectively, in relationship to the antigen content.

The present invention thus also comprises highly purified vWF having a factor VIII-binding capacity of more than 90%, preferably more than 95%, and factor VIII having a vWF binding affinity of at least 90%, respectively. A thus purified vWF or factor VIII/vWF-complex, respectively, may be further purified by means of heparin affinity chromatography, e.g. as described in EP 0 705 846, whereby high-molecular vWF multimers are enriched. The thus obtained vWF or factor VIII/vWF complex, respectively, particularly comprising high-molecular vWF multimers is characterized by a high specific platelet aggregation of at least 60 U/mg protein.

By the method according to the invention, in particular purified vWF or factor VIII/vWF-complex, respectively, is recovered in an aqueous solution containing a zwitterion at a concentration of between 0.08 M and 0.2 M, and at a pH of between 7.3 and 7.8, the zwitterion being selected from the group of the amino acids glycine, alanine, β-alanine, phenylalanine, and histidine, or of the betaines. This purified vWF or factor VIII/vWF-complex then may optionally be subjected to a further virus depletion and/or virus inactivation step known from the prior art.

The purified solution may, e.g. be directly sterile-filtered via-a filter having a pore width of between 100 nM and 0.45 μm, and lyophilized without the addition of a stabilizer, in particular a high-molecular stabilizer.

The method according to the invention may be used for purifying and recovering recombinant or plasmatic vWF or factor VIII/vWF-complex, respectively.

A further object of the present invention relates to a stable preparation containing highly purified vWF or factor VIII/vWF-complex obtainable by immunoaffinity chromatography. According to the present invention, the stable preparation contains vWF having a purity of at least 95%, and a specific antigen-activity of at least 95 U/mg protein, preferably of 100 U/mg protein. A stable preparation provided according to the invention and containing factor VIII/vWF complex has a purity of at least 95%, preferably of 99%, the specific activity of factor VIII:C being at least 95 U/mg protein and that of vWF being at least 95 U/mg protein, the ratio of the specific activity in the complex thus being 1:1.

According to a particular embodiment, the factor VIII/vWF-complex consists of recombinant factor VIII and recombinant vWF, the ratio of factor VIII to vWF being between 0.01 and 100, preferably between 1:30 and 1:70, particularly preferred at approximately 1:50. Within the scope of the invention it has been found that the cell culture supernatants of recombinant vWF- or factor VIII-expressing cells having a defined concentration of antigen can be mixed in a certain, desired ratio, and that after having carried out the method of the invention, purified complex consisting of recombinant proteins can also be recovered again in the desired ratio.

It has been known that during its purification from plasma or from cryoprecipitate, vWF is degraded into low-molecular vWF fragments by proteases possibly present, which fragments then can be identified in SDS gel as low-molecular fraction having satellite bands (Furlan et al., 1993, PNAS. 90: 7503–7507). Furthermore, factor VIII is partly activated by proteases present, whereby the specific activity of the factor VIII/vWF-complex is reduced.

According to a further aspect of the present invention, a stable preparation comprising highly purified vWF or factor VIII/vWF-complex, respectively, is provided, which is particularly characterized in that the molecular and structural integrity of the vWF or of the factor VIII/vWF-complex, respectively, is substantially retained and that it does not contain any proteolytic degradation products of the vWF or activated factor VIII.

According to a further aspect, the preparation according to the invention is substantially free from impurities caused by the immunoadsorbent, the amount of possibly present immunoadsorbent, in particular of antibodies, being less than 15 ng/mg protein, preferably less than 10 ng/mg protein, and particularly preferred less than 7 ng/mg protein. Moreover, the preparation according to the invention is characterized in that it contains less than 3%, preferably less than 1%, fibrinogen and less than 1%, preferably less than 0.5%, fibronectin. The determination of the fibrinogen and fibronectin contents, respectively, there was effected by means of ELISA in accordance with the prior art.

Within the scope of the present invention it has also been shown that particularly by using an eluting agent containing as the essential eluting agent in the buffer an amino acid, such as glycine, histidine or alanine, which hitherto have also been used for stabilizing protein solutions, the eluted vWF or factor VIII/vWF-complex can be kept in a stabilizing environment during the entire purification procedure and thus the preparation obtained is particularly stable.

The preparation according to the invention is stable in solution for a period of at least 2 weeks at 4° C., deep-frozen at –20° C. for at least 6 months, and as a lyophilisate for at least 1 year at a temeprature of from –20° C. to 4° C. By the presence of, e.g., histidine in the eluting agent, furthermore a precipitation of the vWF or factor VIII/vWF-complex, respectively, at lyophilization is prevented. The preparation according to the invention thus may optionally be further processed to a lyophilized product without any further additives. To improve the reconstitution of the lyophilized preparation, arginine may also be admixed, as has been described, e.g., in WO 93/22336. The stable preparation may be formulated for administration to man in a respective manner as a stable pharmaceutical preparation and may contain suitable buffers or physiologically acceptable carriers. As has already been mentioned above, on account of its particularly good stability of the preparation, the addition of a stabilizer optionally can be omitted. It has been known that by the addition of a stabilizer, in particular of HSA, the specific activity of an antigen preparation is reduced, whereby the pharmaceutical composition to be administered has a lower specific activity than the protein preparation recovered directly after purification.

According to the present invention, thus a pharmaceutical composition containing vWF or factor VIII/vWF-complex having a purity of at least 95%, preferably 99%, and a specific activity of vWF of at least 95 U/mg and of factor VIII of at least 95 U/mg is provided which is substantially free-from high-molecular substances and stabilizers, in particular free from HSA. By this, the pharmaceutical preparation according to the invention differs from any hitherto known pharmaceutical compositions which contain substances, such as albumin or heparin, for stabilization thereof.

In principle, no further complex re-formulation of the purified preparation is required for its administration to man, since the purified product can already be recovered from the affinity carrier in a physiologically compatible composition. Likewise, it is already present in the eluate in a stable and stabilized form.

The method according to the invention thus constitutes a simple method for the gentle recovery of highly purified vWF or factor VIII/vWF-complex, respectively, and for the simple production of a stable pharmaceutical preparation, which optionally may be used directly for a therapeutical application.

Before processing the highly purified vWF or vWF-complex, respectively, to a pharmaceutical preparation it is advantageous to carry out an inactivation or depletion of viruses. This may be effected by a chemical and/or physical treatment known in the prior art. Since due to the presence of amino acids, such as glycine, alanine or histidine, contained in the stable preparation according to the invention, vWF or factor VIII/vWF complex is present in a physiological and stabilizing environment, the purified product may, optionally without any further addition of stabilizers, be directly subjected to a virus inactivation step.

The stable preparation provided according to the present invention may be used for producing a medicament for the treatment of hemophilia A or vWD.

DETAILED DESCRIPTION

The invention will be explained in more detail by way of the following examples and the drawing figure, yet it is not restricted to these particular embodiments.

Example 1 describes the determination of the interaction of various anti-vWF-antibodies and vWF by means of surface plasmon resonance and desorption of the antigen from the complex by means of various buffers; Example 2 describes the desorption behaviour of the vWF antigen from the antigen-antibody-complex under different buffer conditions; Example 3 describes the purification of recombinant vWF from cell culture supernatants by means of immunoaffinity; Example 4 describes the purification of plasmatic factor VIII/vWF complex; Example 5 describes the use of an antibody fragment for the immunoaffinity purification of vWF; Example 6 describes the post-purification of immunoaffinity-purified vWF by means of heparin-affinity chromatography; Example 7 describes the influence of the eluting agent on the factor VIII:C activity; Example 8 describes the purification of a complex consisting of recombinant factor VIII and recombinant vWF; Example 9 describes the assaying of the eluate for murine IgG and F'ab fragments, and Example 10 shows the integrity of the factor VIII/vWF-complex in the elution environment according to the invention.

EXAMPLES

General description of methods relating to the test system for determining the interaction of macromolecules By aid of the new technology, the surface plasmon resonance, it has recently become possible to directly follow the interaction of macromolecules, among which there is also the reaction of proteins with specific antibodies (Karlsson, 1994, Analyt. Biochem. 221: 142–151; Malmqvist, 1993, Nature 361; 186–187).

In an optical system that is in direct contact with the sample to be examined, a parameter dependent on the molecule concentration is measured and is expressed in so-called response units (RU). High RU values correspond to a high concentration of adsorbed macromolecules on the measured surface (sensor chip).

The advantages of this method are that little substance is consumed, that it can be carried out rapidly and that the data can be evaluated kinetically. By aid of this measuring system, the basic binding properties of vWF-specific antibodies have been examined.

Example 1

Determination of the interaction of various anti-vWF-antibodies and vWF by means of surface plasmon resonance and desorption of the antigen from the complex with different buffers Monoclonal anti-vWF-antibodies (Immunotech, Marseille) were bound to the active layer of a CM sensor chip by means of the standard method described by Pharmacia. As the negative controls, a lane of the sensor chip was coated with a monoclonal antibody to Pseudomonas Flagellin (PAM 24). The effectivity of coupling can be recognized from the increase of the signal. After coupling, the lanes of the sensor chip were washed with 3 M NaSCN so as to remove non-specifically adsorbed antibody from the chip surface. vWF (pre-purified via anion exchange chromatography) subsequently was led over the chip surface (adsorption phase). After a washing procedure with Tris buffer, pH 7.4, various buffers containing 100 mM glycine and with increasing pH values of from pH 6.0 to pH 9.0 were led over the chip (elution phase). Table 1 shows the determination of the interaction of various anti-vWF-antibodies and vWF by means of surface plasmon resonance and desorption of the antigen from the complex with glycine buffer with different pH values.

TABLE 1

| Lane | vWf loading (RU) | | Glycine elution | | | | | | | |
|---|---|---|---|---|---|---|---|---|---|---|
| | | | pH 6 | | pH 7 | | pH 8 | | pH 9 | |
| | r-vWF | pdvWF | r-vWF | pdvWF | r-vWF | pdvWF | r-vWF | pdvWF | r-vWF | pdvWF |
| AvW8-1 | 650 | 490 | 145 | 220 | 40 | 65 | 15 | 20 | 10 | 20 |
| AvW8-2 | 870 | 760 | 75 | 125 | 25 | 50 | 10 | 15 | 15 | 12 |
| PAM 24 | 12 | 25 | 10 | 15 | 10 | 15 | 10 | 15 | 10 | 15 |
| blank lane | 14 | 35 | −5 | 5 | −20 | 5 | −20 | 5 | −20 | 5 |

According to the disclosure by Mejan et al. (1988, Thromb. Haemost. 59: 364–371), the maximum affinity between antibody and antigen is between pH 5 and 7. Thus, it could not be expected that as of a pH of 6.0 there would be a marked detachment of the adsorbed rvWF. The change in the desorption behaviour of the antigen-antibody-complex was attributed to the presence of glycine in the buffer. Furthermore, it has been shown that the two different-anti-vWF-antibodies AvW8-1 and AvW8-2 have the same behaviour relative to glycine.

To exclude that the effect obeserved was a particular property of recombinant vWF, the experiment was repeated with plasmatic vWF (pdvWF), yielding the same result.

Example 2

Desorption behaviour of the vWF antigen from the antigen-antibody-complex under different buffer conditions To more closely examine the nature of the vWF-antigen/anti-vWF-antibody interaction, further elution tests were carried out with different buffers/eluting agents. Above all, the efficacy of buffers containing different amino acids or the derivatives thereof at pH 7.4 were examined.

Among the substances tested there were i.a.alanine, β-alanine, phenylalanine, histidine, arginine, lysine, glutamic acid, aspartic acid, betaine and acetate.

Table 2 shows the determination of the interaction of anti-vWF-antibodies and vWF antigen by means of surface plasmon resonance and desorption of the antigen from the complex by means of buffers containing different amino acids as the elution reagent.

TABLE 2

| Amino acid | RU before elution | RU after elution | % eluted |
|---|---|---|---|
| Alanine | 850 | 25 | 97 |
| β-Alanine | 830 | 30 | 97 |
| Phenylalanine | 520 | 25 | 95 |
| Histidine | 550 | 15 | 97 |
| Arginine | 970 | 780 | 20 |
| Lysine | 840 | 730 | 13 |
| Glutamic acid | 760 | 720 | 5 |
| Aspartic acid | 670 | 590 | 12 |
| Betaine | 680 | −10 | 100 |
| Acetate | 570 | 550 | 3 |

It has been found that particularly amino acids having non-polar groups, such as glycine, alanine, alanine or phenylalanine, or derivatives thereof or amino acids present as zwitterions in the neutral range, such as histidine, are capable of effectively eluting the vWF bound to the antibody (Table 2).

Respective buffers containing these amino acids or derivatives thereof for the purification of vWF or of vWF/factor VIII-complex were tested by means of immunoaffinity chromatography.

Example 3

Purification of recombinant vWF from cell culture supernatants by means of immunoaffinity (at present considered by applicant to be the best mode of carrying out the invention)

Monoclonal anti-vWF-antibody AvW8-2 was covalently coupled to CNBr-activated Sepharose (Pharmacia) according to the producer's instructions. There, the loading of the resin with antibody amounted to 1 mg/ml packed gel.

500 ml of a concentrated fermentation supernatant containing recombinant vWF (rvWF) were applied at a linear flow rate of 20 cm/h to a column filled with 50 ml affinity resin. After the sample had been applied, the column was rinsed with phosphate buffer, pH 7.4, until the UVW absorption of the column effluent had reached the base line value. Bound rvWF was eluted from the column by slow (5 cm/h) elution with 100 mM glycine, pH 7.4.

In table 3, the analytical data of the corresponding fractions are illustrated

TABLE 3

| Sample | vWF Ag (ELISA) µg/ml | % | Ristocetin activity U/ml | % | Protein µg/ml | % | Spec. Activity | |
|---|---|---|---|---|---|---|---|---|
| | | | | | | | mg Ag mg Prot | U RCoA mg Prot |
| Starting material | 120 | 100 | 1.5 | 100 | 1400 | 100 | 0.08 | 1.07 |
| Adsorbate | 10 | 9 | <0.02 | <7 | 1220 | 96 | 0.008 | <0.02 |
| Eluate | 370 | 74 | 5.0 | 80 | 350 | 6 | 1.06 | 14.2 |

From these results it is apparent that under the conditions indicated, recombinant vWF can be obtained from fermentation supernatants in good yields, in high purity, having a specific antigen activity of at least 100 U/mg protein and with at least 74% recovery.

Example 4

Purification of plasmatic FVIII/vWF complex 50 g of cryoprecipitate were dissolved in 450 ml of heparin buffer. The factors of the prothrombin complex were removed by the addition of 0.1% alhydrogel. The clarified protein solution is purified as described in Example 3 by means of immunoaffinity. In Table 4, the analytical data before and after purification are summarized.

TABLE 4

| Sample | vWF Ag (ELISA) µg/ml | % | FVIII-Activity U/ml | % | Protein mg/ml | % | Spec. Activity mg vWF/mg Prot | Spec. Activity FVIII:C U/mg Prot |
|---|---|---|---|---|---|---|---|---|
| Starting material | 230 | 100 | 16 | 100 | 21 | 100 | 0.01 | 0.76 |
| Adsorbate | 10.3 | 6 | 1.1 | 9 | 15.2 | 98 | 0.00 | 0.07 |
| Eluate | 320 | 68 | 25.5 | 78 | 0.27 | 0.9 | 1.18 | 94 |

From Table 4 it is apparent that when using cryoprecipitate as the starting material, a FVIII/vWF-complex having a high purity, a specific activity of vWF of at least 118 antigen-U/mg protein and of factor VIII of at least 94 U/mg can be recovered. By the method according to the invention, free factor VIII is removed, and substantially pure factor VIII/vWF-complex is recovered at a ratio of approximately 1:1. The yield of pure factor VIII/vWF-complex is approximately between 70% to 80% and thus above the values hitherto described for the protein recovery by means of immunoaffinity chromatography.

Example 5

Use of an antibody fragment for immunoaffinity purification of vWF

In the same manner as the intact monoclonal antibody, also a F'ab- or F'ab2-fragment of the monoclonal antibody can be used. This mode of procedure has the advantage that traces of the antibody possibly present in the final product do no longer contain an immunologically active protein portion (Fc-portion).

Fragmentation of the antibody may be effected by selective proteases, such as papain or pepsin (in free form or bound to an insoluble carrier substance). In the following, the preparation, purification and use of an F'ab-fragment from the monoclonal antibody AvW8-2 is described:

100 mg of the monoclonal antibody AvW8-2 were admixed with 1 mM cysteine. To this solution, 0.5 mg of immobilized papain (Pierce) were added, and the suspension was incubated for 5 h at 37° C. The protease digestion was stopped by filtering off the immobilized papain, a possible residual activity was inhibited by the addition of 10 mM iodoacetamide. The separation of the F'ab-fragments from Fc-fragments, smaller fragments and intact antibody was effected by means of anion exchange chromatography on Poros Q. Purified F'-ab-fragments were coupled to CNBr-activated Sepharose at a loading density of 1 mg/ml gel. 500 ml of a concentrated fermentation supernatant containing rvWF were purified as described in Example 3 by means of 50 ml of the thus-prepared affinity resin.

Table 5 shows the results of the immunoaffinity chromatograpy by means of elution with a buffer containing 100 mM glycine, pH 7.4.

TABLE 5

| Sample | vWF Ag (ELISA) µg/ml | % | Ristocetin activity U/ml | % | Protein µg/ml | % | Spec. Activity mg Ag/mg Prot | U RCoA/mg Prot |
|---|---|---|---|---|---|---|---|---|
| Starting material | 105 | 100 | 1.8 | 100 | 1250 | 100 | 0.08 | 1.44 |
| Adsorbate | 9 | 9 | <0.02 | <8 | 1200 | 105 | 0.00 | <0.02 |
| Eluate | 248 | 85 | 3.8 | 76 | 265 | 4 | 0.93 | 14.3 |

From the results given in Table 5 it is apparent that for the immunoaffinity-chromatographic purification of vWF, an F'ab-fragment of the monoclonal antibody can be used with the same efficiency as the intact antibody. However, vWF could be recovered with an improved yield of 85% of the starting material and a specific activity of at least 93 antigen-U/mg protein.

Example 6

Post-purification by means of heparin affinity chromatography

It is possible to further improve the quality of the thus purified vWF, be it by enrichment of vWF multimers consisting of high-molecular vWF multimers, or by eliminating residual contaminations, in a further purification step. As methods for this, the known methods, such as ion exchange chromatography, heparin affinity chromatography or gel filtration can be used.

In the following, the combination of the immunoaffinity chromatography with a subsequent heparin chromatography will be described.

The eluate of the immunoaffinity chromatography (Example 5) is loaded without any further treatment onto a 50 ml column filled with Fractogel®-heparin. Elution of the bound rvWF is effected by applying a step-like salt gradient, rvWF mainly being eluted in a range of between 0.25 M and 0.3 M NaCl.

All chromatographic buffers contain 100 mM glycine so as to ensure the dissociation of possibly leaked F'ab-fragments of vWF during the heparin chromatography. The results of the heparin affinity chromatography are summarized in Table 6.

TABLE 6

| Sample | vWF Ag (ELISA) µg/ml | % | Ristocetin activity U/ml | % | Protein µg/ml | % | Spec. Activity mg Ag/mg Prot | U RCoA/mg Prot |
|---|---|---|---|---|---|---|---|---|
| Starting material | 250 | 100 | 3.8 | 100 | 265 | 100 | 0.94 | 14.3 |
| Adsorbate | 95 | 46 | <0.02 | <4 | 105 | 48 | 0.9 | <0.19 |
| Step 1 | 85 | 15 | 0.8 | 9 | 89 | 14 | 0.96 | 9.0 |
| Step 2 | 115 | 19 | 7.8 | 85 | 125 | 20 | 0.92 | 62.4 |

As can be seen from Table 6, the ristocetin activity of vWF can be further improved by subsequent purification steps. It has particularly been found that a specific platelet agglutinating activity of more than 60 U/mg protein is obtained. Moreover, more than 85% of the material used can be recovered as a purified protein having a high specific activity.

After sterile filtration and pharmaceutical formulation, the final product of the purification can be filled into the respective final containers and lyophilized. In this instance, the glycine contained in the buffer will serve as the stabilizing agent during the lyophilisation and dissolving procedures.

Example 7

Influence of the eluting agent on FVIII:C-activity

Dissolved cryobulin was adsorbed, as described in Example 4, on a column loaded with AvW8-2. In that instance, coupling of the antibody was effected via benzoquinone so as to improve the pH stability. Elution of the bound FVIII/vWF-complex was effected by raising the pH, on the one hand, as described in Mejan et al. (1988, Thromb. Haemost. 59: 364–371), and by glycine-elution according to the method of the invention, on the other hand.

In Table 7, the results of the determination of the yield and of the specific factor VIII activity by means of immunoaffinity chromatography with different elution methods are summarized.

TABLE 7

| Elution method | Spec. activity U FVIII: C mg protein | Yield FVIII: C % |
|---|---|---|
| pH-Shift | 37 | 21 |
| Glycine | 67 | 82 |

From Table 7 it is apparent that when using glycine buffer as the eluting agent, the yield can be increased up to the 4-fold as compared to the pH shift, and the specific activity of the recovered factor VIII can be doubled. The reason for this seems to be the exposure or the activation, respectively, of FVIII at a pH-shift, while under mild elution conditions and at a neutral pH in the presence of an amino acid or of the zwitterion, respectively, the activity of factor VIII is less impaired.

Example 8

Purification of a complex consisting of recombinant FVIII and recombinant vWF

Cell culture supernatants from recombinant cells, transfected with a vector containing cDNA encoding factor VIII or vWF, respectively, were mixed at a ratio of 3 factor VIII: 1 vWF. The mixture containing rFVIII/rvWF-complex was purified under conditions as stated in Example 3.

In Table 8 the results of this purification of rfactor VIII/rvWF are illustrated.

TABLE 8

| Sample | U FVIII: C/ml | Yield FVIII: C | µg vWF/ml | Yield vWF | U FVIII: C U vWF |
|---|---|---|---|---|---|
| Applied. material | 2.1 | 100 | 6.1 | 100 | 3.4 |
| Effluent | 0.4 | 19 | neg. | 0 | n.d.* |
| Glycine eluate | 8.3 | 73 | 25.7 | 67 | 3.2 |

*n.d. = not determined

Table 8 shows that under the conditions indicated, a complex consisting of rFVIII and rvWF behaves just like a plasmatic complex. Likewise, rFVIII/rvWF-complex was recovered in a certain ratio to each other depending on the mixing ratio of the starting material. By varying the FVIII/vWF ratio in the starting material or by following up with a further chromatographic step, the ratio of FVIII:C to vWF can furthermore be varied in favour of the relative FVIII content. By this it is possible to purposefully obtain a factor VIII/vWF-complex having a certain desired ratio.

Example 9

Assay for murine IgG (F'ab-fragments)

Contaminating F'ab-fragments in the eluate of the immunoaffinity column were detected by aid of an immunological method (Immuno Ligand Assay, Molecular Devices).

Rabbit-anti-mouse-IgG (F'ab-specific) is labelled with biotin or fluorescein. 100 µl of the column eluate are mixed with 2 µg of each of the biotin- and the fluorescein-labelled antibody and incubated. After a further incubation with 2 µg of streptavidine and urease-labelled anti-fluorescein-antibody, the mixture is filtered through a biotinylated membrane. After washing of the membrane, bound F'ab-fragment can be detected with a high sensitivity (approximately 100 pg/ml).

In Table 9, the results of various chromatographic runs are summarized.

TABLE 9

| Sample | Elution Method | vWF-Antigen µg/ml | Murine IgG ng/ml | ng Murine IgG mg vWF Antigen |
|---|---|---|---|---|
| Cryoprecipitate | pH-shift* | 280 | 34.5 | 123.2 |
| Recomb. vWF | pH-Shift* | 190 | 28.6 | 150.5 |
| Cryoprecipitate | Glycine | 320 | 4.2 | 13.1 |
| Recomb. vWF | Glycine | 248 | 1.9 | 7.6 |

*Coupling of the antibody was effected via benzoquinone in this instance so as to attain a better pH stability.

From Table 9 it can be seen that with the method according to the invention it is possible to recover vWF or factor VIII/vWF-complex, respectively, with very low amounts of contaminating murine IgG (F'ab-fragments).

By adding a further chromatographic purification step (heparin chromatography or ion exchange chromatography) it is possible to reduce this residual contamination to below the detection limit.

Example 10

Integrity of the purified FVIII/vWF-complex

Figure 1:
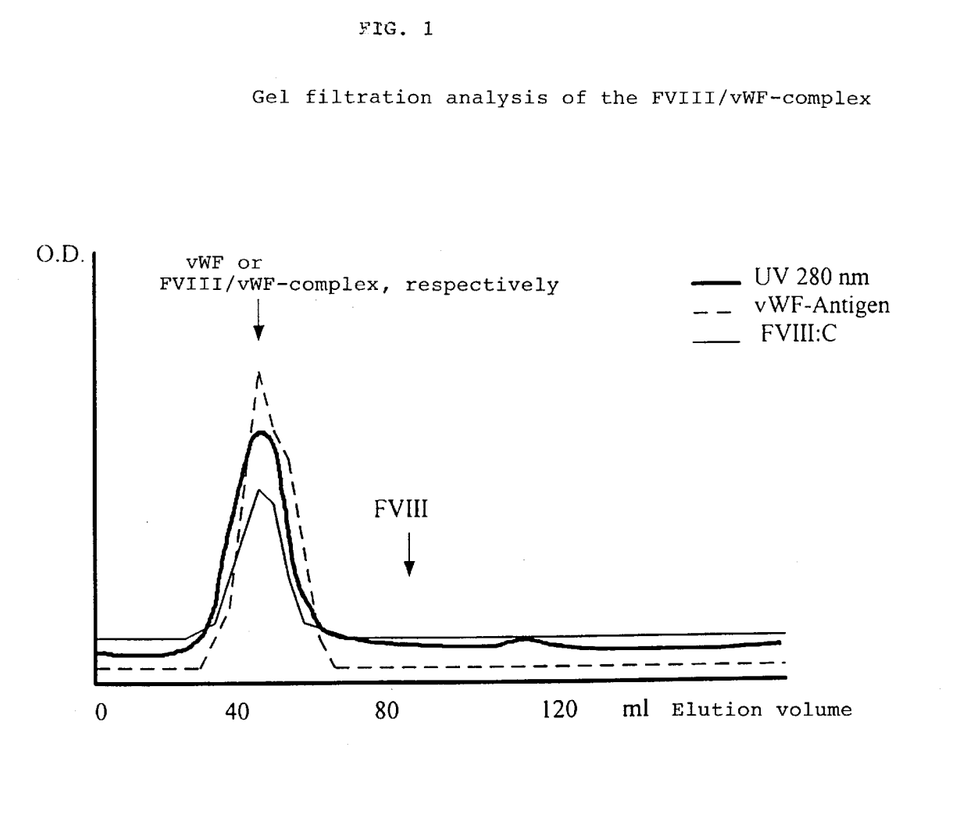
FIG. 1 shows a gel filtration analysis of the factor VIII/vWF-complex.

To demonstrate the integrity of the purified complex consisting of FVIII and vWF, 5 ml of the eluate of the immunoaffinity column, obtained according to Example 4, were applied to a gel filtration column filled with 120 ml Sepharose CL6B. By elution with glycine buffer as the running solvent, there occurs a aseparation according to the molecular size during the chromatographic run.

Based on the separation characteristics of the column material, a separation of both proteins would occur if two different molecule species (FVIII and vWF) were present. In FIG. 1, the results of this chromatographic run are illustrated.

It can be recognized clearly that the complex of FVIII and vWF obtained according to Example 4 appears in a peak (▬). If the two proteins were not associated, they would eluate clearly separately from each other (cf. labelling).

FVIII/vWF-complex purified according to the method of the invention thus is present as a protein complex in which the vWF takes on the task of stabilizing FVIII.

What is claimed is:

1. A method of recovering highly purified von Willebrand factor (vWF) or factor VIII/vWF-complex by means of immunoaffinity chromatography, said method comprising
   (a) binding a vWF or a factor VIII/vWF complex to an immunoadsorbent, and
   (b) eluting said bound vWF or factor VIII/vWF-complex from said immunoadsorbent with an eluting agent comprising a zwitterion, said eluting performed in the absence of a chaotropic agent whereby said vWF or factor VIII/vWF-complex retains its molecular integrity.

2. A method as set forth in claim 1, wherein said zwitterion is selected from the group consisting of neutral amino acids and betaines.

3. A method as set forth in claim 2, wherein said neutral amino acids are selected from the group consisting of glycine, alanine, β-alanine, phenylalanine and histidine.

4. A method as set forth in claim 1, wherein said zwitterion is present in said eluting agent at a concentration above 0.05 M and no greater than 0.05 M.

5. A method as set forth in claim 4, wherein said concentration of said zwitterion ranges between 0.08. and 0.2 M.

6. A method as set forth in claim 4, wherein said concentration of said zwitterion ranges between 0.1 and 0.15 M.

7. A method as set forth in claim 1, wherein said eluting agent has a physiological pH.

8. A method as set forth in claim 7, wherein said physiological pH of said eluting agent ranges between 7.0 and 8.0.

9. A method as set forth in claim 7, wherein said physiological pH of said eluting agent ranges between 7.3 and 7.8.

10. A method as set forth in claim 7, wherein said physiological pH of said eluting agent is 7.4.

11. A method as set forth in claim 1, wherein said immunoadsorbent is an anti-vWF-antibody.

12. A method as set forth in claim 11, wherein said anti-vWF-antibody is a monoclonal antibody.

13. A method as set forth in claim 1, wherein said immunoadsorbent is a fragment of an anti-vWF-antibody.

14. A method as set forth in claim 1, wherein eluted vWF or factor VIII/vWF-complex is present in an aqueous solution comprising said zwitterion at a concentration of between 0.08 M and 0.2 M and having a pH of between 7.3 and 7.8, said zwitterion being selected from the group consisting of neutral amino acids and betaines.

15. A method as set forth in claim 14, wherein said neutral amino acids are selected from the group consisting of glycine, alanine, β-alanine, phenylalanine and histidine.

16. A method as set forth in claim 14, further comprising lyophilizing said purified vWF or factor VIII/vFW-complex without addition of high molecular weight stabilizers.

17. A method as set forth in claim 1, further comprising subjecting said eluted vWF or factor VIII/vWF-complex to a filer chromatographic step.

18. A method as set forth in claim 17, wherein said further chromatographic step is heparin affinity chromatography.

19. A method as set forth in claim 1, further comprising subjecting said eluted vWF or factor VIII/vWF-complex to at least one of a virus inactivation step or a virus depletion step.

20. A method as set forth in claim 1, wherein said zwitterion is present in said eluting agent at a concentration of between 0.08 and 0.5 M.

21. A preparation comprising highly purified von Willebrand Factor (vWF) having a specific activity of at least 100 U/mg of protein.

22. A preparation as set forth in claim 21, wherein said preparation is stable in solution at 4° C. for at least 2 weeks, deep-frozen at −20° C. for at least 6 months, and as a lyophilisate for at least one year.

23. A preparation as set forth in claim 21, wherein said preparation is substantially free from any immunoadsorbent-caused impurities.

24. A preparation as set forth in claim 23, wherein said impurities are caused by an antibody or a fragment of an antibody.

25. A preparation as set forth in claim 21, comprising less than 15 ng of murine IgG/mg of protein.

26. A preparation as set forth in claim 21, comprising less than 10 ng of murine IgG/mg of protein.

27. A preparation as set forth in claim 21, comprising less than 7 ng of murine IgG/mg of protein.

28. A preparation as set forth in claim 21, said preparation having been subjected to at least one virus inactivation step.

29. A preparation as set forth in claim 21, comprising less than 3% of fibrinogen and less than 1% of fibronectin.

30. A preparation as set forth in claim 21, comprising less than 1% of fibrinogen and less than 0.05% of fibronectin.

31. A preparation as set forth in claim 21, wherein said preparation is formulated as a pharmaceutical composition.

32. A preparation as set forth in claim 31, wherein said preparation has a purity of at least 95% and a specific activity of factor VIII of at least 95 U/mg and of vWF of at least 95 U/mg.

33. A preparation as set forth in claim 32, wherein said purity amounts to 99%.

34. A preparation as set forth in claim 32, said preparation being free from high-molecular weight stabilizers.

35. A preparation comprising less than 3% of fibrinogen and less than 1% of fibronectin and factor VIII/von Willebrand Factor (vWF) complex having a purity of at least 95% and a specific activity of factor VIII of at least 95 U/mg of protein, and of vWF:Ag (vWF:antigen) of at least 95 U/mg of protein.

36. A preparation as set forth in claim 35, wherein said purity of said factor VIII/vWF-complex is 99%.

37. A preparation as set forth in claim 35, wherein said vWF and said factor VIII contained in said factor VIII/vWF complex are a recombinant vWF and a recombinant factor VIII, the molar ratio of factor VIII to vWF ranging between 0.01 and 100.

38. A preparation as set forth in claim 37, wherein said molar ratio of factor VIII to vWF ranges between 1:30 and 1:70.

39. A preparation as set forth in claim 37, wherein said molar ratio of factor VIII to vWF is approximately 1:50.

40. A preparation as set forth in claim 35, wherein said preparation is stable in solution at 4° C. for at least 2 weeks, deep-frozen at −20° C. for at least 6 months, and as a lyophilisate for at least one year.

41. A preparation as set forth in claim 35, wherein said preparation is substantially free from any immunoadsorbent-caused impurities.

42. A preparation as set forth in claim 41, wherein said impurities are caused by an antibody or a fragment of an antibody.

43. A preparation as set forth in claim 35, comprising less than 15 ng of murine IgG/mg of protein.

44. A preparation as set forth in claim 35, comprising less than 10 ng of murine IgG/mg of protein.

45. A preparation as set forth in claim 35, comprising less than 7 ng of murine IgG/mg of protein.

46. A preparation as set forth in claim 22, said preparation having been subjected to at least one virus inactivation step.

47. A preparation as set forth in claim 35, comprising less than 3% of fibrinogen and less than 1% of fibronectin.

48. A preparation as set forth in claim 35, comprising less than 1% of fibrinogen and less than 0.5% of fibronectin.

49. A preparation as set forth in claim 22, wherein said preparation is formulated as a pharmaceutical composition.

50. A method of treating a patient suffering from one of von Willebrand Factor (vWF) and phenotypic hemophilia A by administering to said patient an effective dose of a highly pure vWF-containing preparation having a specific activity of at least 100 U/mg of protein.

51. A method of treating a patient suffering from one of von Willebrand Factor (vWF) and phenotypic hemophilia A by administering to said patient an effective dose of a factor VIII/vWF complex-containing preparation having a purity of at least 95% and a specific activity of factor VIII of at least 95 U/mg of protein and of vWP:Ag (vWF:antigen) of at least 95 U/mg of protein and comprising less than 3% fibrinogen and less than 1% fibronectin.

\* \* \* \* \*

UNITED STATES PATENT AND TRADEMARK OFFICE
CERTIFICATE OF CORRECTION

PATENT NO. : 6,579,723 B1  Page 1 of 1
DATED : June 17, 2003
INVENTOR(S) : Artur Mitterer et al.

It is certified that error appears in the above-identified patent and that said Letters Patent is hereby corrected as shown below:

Column 1,
Line 4, please insert the following text after the title:

-- CROSS-REFERENCES TO RELATED APPLICATIONS
This application is the U.S. national phase of PCT/AT98/00033, filed February 18, 1998, which claims priority of Austrian Application A339/97, filed February 27, 1997. --

Column 4,
Line 5, the phrase "vWFor" should read -- vWF or --;
Lines 37-38, the phrase "analogues of amito acids, preferably alanine, ß-alanine, 2-amino-butyrid acid," should read -- analogues of amino acids, preferably alanine, ß-alanine, 2-amino-butyric acid, --.

Column 16,
Line 54, "aseparation" should read -- separation --.

Column 17,
Line 53, "filer" should read -- further --.

Column 18,
Line 64, "claim 22" should read -- claim 35 --.

Column 19,
Line 3, "claim 22" should read -- claim 35 --.

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,579,723 B1
DATED : June 17, 2003
INVENTOR(S) : Artur Mitterer et al.

It is certified that error appears in the above-identified patent and that said Letters Patent is hereby corrected as shown below:

Column 18,
Lines 66-67, delete entire claim

Signed and Sealed this

Seventh Day of December, 2004

JON W. DUDAS
*Director of the United States Patent and Trademark Office*